(12) United States Patent
Okamoto et al.

(10) Patent No.: US 7,858,806 B2
(45) Date of Patent: Dec. 28, 2010

(54) CRYSTAL FORM OF 5-HYDROXY-1-METHYLHYDANTOIN

(75) Inventors: Kaoru Okamoto, Hyogo (JP); Naoharu Nishimura, Hyogo (JP); Akira Ishii, Hyogo (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 12/498,967

(22) Filed: Jul. 7, 2009

(65) Prior Publication Data

US 2009/0270634 A1 Oct. 29, 2009

Related U.S. Application Data

(63) Continuation of application No. 10/508,496, filed as application No. PCT/JP03/04497 on Apr. 9, 2003, now Pat. No. 7,569,701.

(30) Foreign Application Priority Data

Apr. 10, 2002 (JP) .............................. 2002-107533

(51) Int. Cl.
C07D 233/80 (2006.01)
(52) U.S. Cl. ................................. 548/317.5
(58) Field of Classification Search .................. 514/390; 548/317.5
See application file for complete search history.

(56) References Cited

U.S. PATENT DOCUMENTS

| | | | |
|---|---|---|---|
| 4,281,009 A | 7/1981 | Konishi | |
| 4,647,574 A | 3/1987 | Ienaga et al. | |
| 4,935,507 A | 6/1990 | Takaya et al. | |
| 4,985,453 A | 1/1991 | Ishii et al. | |
| 5,084,473 A | 1/1992 | Mikami et al. | |
| 5,120,850 A | 6/1992 | Bod et al. | |
| 5,294,615 A | 3/1994 | Meyer et al. | |
| 5,294,636 A | 3/1994 | Edwards et al. | |
| 5,352,694 A | 10/1994 | Cuthbert | |
| 5,412,095 A | 5/1995 | Morley et al. | |
| 5,681,843 A | 10/1997 | Kotani et al. | |
| 6,040,326 A | 3/2000 | Hotta et al. | |
| 6,197,806 B1 | 3/2001 | Endou et al. | |
| 6,251,929 B1 | 6/2001 | Naiki et al. | |
| 6,451,831 B1 | 9/2002 | Ienaga et al. | |
| 7,569,701 B2 * | 8/2009 | Okamoto et al. | 548/317.5 |
| 2006/0241162 A1 | 10/2006 | Okamoto et al. | |
| 2006/0241163 A1 | 10/2006 | Okamoto et al. | |

FOREIGN PATENT DOCUMENTS

| | | |
|---|---|---|
| JP | 57-114578 | 7/1982 |
| JP | 60-188373 | 9/1985 |
| JP | 61-043168 | 3/1986 |
| JP | 61-122275 | 6/1986 |
| JP | 61-212567 | 9/1986 |
| JP | 62-045525 | 2/1987 |
| JP | 1-299276 | 12/1989 |
| JP | 3-072463 | 3/1991 |
| JP | 4-342556 | 11/1992 |
| JP | 7-149732 | 6/1995 |
| JP | 8-269018 | 10/1996 |
| JP | 9-227377 | 9/1997 |
| JP | 10-072446 | 3/1998 |
| JP | 11-171843 | 6/1999 |
| JP | 2000-212083 | 8/2000 |
| JP | 2002-241283 | 8/2002 |
| JP | 2004-123735 | 4/2004 |
| JP | 2004-123736 | 4/2004 |

OTHER PUBLICATIONS

Haleblian, et al. Journal of Pharmaceutical Sciences. (1969), 58, pp. 911-925.*
Concise Encyclopedia Chemistry (1993) Walter de Gruyter Berlin-New York.*
Zaugg, et al. Journal of Heterocyclic Chemistry (1974), 11 (5), pp. 833-834.*
U.S. Appl. No. 11/110,267, filed Apr. 20, 2005, Okamoto et al.
U.S. Appl. No. 11/110,111, filed Apr. 20, 2005, Okamoto et al.
Byrn, et al., "Comparing X-Ray Powder Data", Solid State Chemistry of Drugs, 2nd edition, p. 63.
Ienaga et al., "Bioactive Compounds Produced In Animal Tissues (II); Two Hydantoin Plant Growth Regulators Isolated From Inflamed Rabbit Skin Tissue", Tetrahedron Letters, vol. 28, No. 39, pp. 4587-4588, 1987.
Ienaga et al., "The Stepwise Mammalian Oxidation of the Hydantoin 1-Methylimidazolidine-2,4-dione into Methylimidazalidinetrione via 5-Hydroxy-1-methyl-imidazolidine-2,4-dione", J. Chem. Soc., Perkin Trans. 1, pp. 1153-1156, 1989.
Meanwell et al., "Diethyl 2,4•Dioxylimidazolidine•t•phosphonates: Homer-Wadsworth-Emmons Reagents for the Mild and Efficient Preparation of C-5 Unsaturated Hydantoin Derivatives", J. Org. Chem., vol. 56, No. 24, pp. 6897-6904, 1991.

* cited by examiner

*Primary Examiner*—Rebecca L Anderson
*Assistant Examiner*—Shawquia Young
(74) *Attorney, Agent, or Firm*—Greenblum and Bernstein, P.L.C.

(57) ABSTRACT

Conventional I-form crystals of 5-hydroxy-1-methylhydantoin contain, remaining therein in a considerable amount, the organic solvent used in a purification step. In contrast, in II-form crystals, the amount of the organic solvent remaining therein is smaller than the detection limit. Namely, the II-form crystals contain substantially no residual organic solvent. The novel II-form crystals of 5-hydroxy-1-methylhydantoin obtained through recrystallization from water not only contain substantially no residual organic solvent, but also have a high bulk density and are hence advantageous for pharmaceutical preparation. They further have properties advantageous for production, such as low adhesion. The crystals are significantly useful as a material for medicines required to have high safety, such as drugs for renal insufficiency.

10 Claims, 2 Drawing Sheets

CRYSTAL FORM OF 5-HYDROXY-1-METHYLHYDANTOIN

This application is a continuation of U.S. application Ser. No. 10/508,496 filed Apr. 9, 2003, now U.S. Pat. No. 7,569,701. which is a 371 U.S. national stage application of International Application No. PCT/JP03/04497 filed Apr. 9, 2003, which claims priority of Japanese patent application 2002-107533 filed Apr. 10, 2002. The disclosures of said U.S. application Ser. No. 10/508,496 and said International Application No. PCT/JP03/04497 are incorporated by reference herein in their entireties.

TECHNICAL FIELD

The present invention relates to a novel crystal form of 5-hydroxy-1-methylimidazolidin-2,4-dione (hereinafter, referred to as 5-hydroxy-1-methylhydantoin) and also to a process for producing the same.

BACKGROUND ART

It has been known that 5-hydroxy-1-methylhydantoin is useful as plant growth regulator (Japanese Patent Laid-Open No. Sho-57-114578), hypoglycemic agent, diuretic (Japanese Patent Laid-Open No. Sho-60-188373), hypolipemic agent (Japanese Patent Laid-Open No. Sho-6245525), improving agent for renal function (Japanese Patent Laid-Open No. Hei-03-72463), eliminating agent for active oxygen and free radical (Japanese Patent Laid-Open No. Hei-09-227377), therapeutic agent for intractable vasculitis (Japanese Patent Laid-Open No. 2000-212083), agent for hypoaqlbuminaemia (Japanese Patent Laid-Open No. 2002-241283), etc. and a process for producing the compound is disclosed in Japanese Patents Laid-Open Nos. Sho-57-114578, Sho-60-188373 and Sho-61-122275. In the process for the production disclosed in the above-mentioned gazettes, 5-hydroxy-1-methylhydantoin is recrystallized from ethyl acetate.

When the samples which were recrystallized from organic solvents such as ethyl acetate, acetonitrile, acetone, a mixture of ethanol and hexane, a mixture of tetrahydrofuran and chloroform, etc. were analyzed by means of infrared spectrophotometry or X-ray powder diffraction method, all cases gave the same crystal form and it has been believed that there is no crystal polymorphic form of 5-hydroxy-1-methylhydantoin. As a result of analyses of the residual solvent in the crystal form obtained by recrystallization from acetone, about 1,300 to 1,700 ppm of acetone was detected as a residual solvent. Under such circumstances, investigations were conducted for a method of removing the residual solvent using drying by heating, drying by means of spray-drying method or the like, but its removal has not been successful.

As to the compounds used as drugs, it is preferred that toxic residual solvent are made as small as possible. Especially in patients suffering from renal failure, waste products and toxic substances are not excreted but accumulated in the body due to the disorder of renal functions and, therefore, toxic residual solvent or the like is to be made as little as possible in drugs such as that for renal failure. However, as mentioned above, considerable amount of solvent for recrystallization remains when 5-hydroxy-1-methylhydantoin is recrystallized from organic solvent such as acetone or ethyl acetate and, therefore, that is not preferred as a material for drugs, particularly the drug for renal failure, which are demanded to be highly safe. Accordingly, there has been a demand for obtaining a pure product which substantially contains no residual solvent.

DISCLOSURE OF THE INVENTION

Up to now, 5-hydroxy-1-methylhydantoin has been recrystallized from an organic solvent such as ethyl acetate or acetone. The reason is that, since the compound is very easily soluble in water, its recrystallization from water has been contrary to the common knowledge. However, as a result of various investigations for the preparation of pure product of 5-hydroxy-1-methylhydantoin which is more suitable as a drug, the present inventors have found that, when only one-half amount water of 5-hydroxy-1-methylhydantoin is used, it makes the recrystallization possible and such recrystallization have succeeded in preparing a pure product where organic solvent is not substantially remained.

As mentioned already, it has been already confirmed that 5-hydroxy-1-methylhydantoin obtained by recrystallization from various organic solvents has the same crystal form (hereinafter, referred to as "I-form crystals"). However, it has now been found that the crystals obtained by recrystallization from water in a large-scale synthesis are in a novel crystal form (hereinafter, referred to as "II-form crystals") being different from the conventional I-form crystals as a result of analysis of infrared spectrophotometry and X-ray powder diffraction measurement. The novel II-form crystals not only has no substantial residual organic solvent but also has preferred characteristics in its manufacture such as that it has a sufficient stability, its bulk density is high being advantageous for making into pharmaceutical preparations and its adhesive property is low. An object of the present invention is to provide a novel crystal form of 5-hydroxy-1-methylhydantoin containing substantially no residual organic solvent, being highly safe as drugs and being suitable for the production and for making into pharmaceutical preparations.

The present invention relates to a novel crystal form of 5-hydroxy-1-methylhydantoin where there is substantially no residue of organic solvent. Here, the expression reading "substantially no residue of organic solvent" means that the residual organic solvent is not more than the detection limit (1 ppm) when the measurement is carried out according to a conventional method for the measurement of residual organic solvent such as a gas chromatography mentioned in "Test Method for Residual Solvent" of the Japanese Pharmacopoeia (14th edition).

BEST MODE FOR CARRYING OUT THE INVENTION

The novel crystal form (II-form crystals) of 5-hydroxy-1-methylhydantoin of the present invention can be manufactured according to the following recrystallization method. Thus, 5-hydroxy-1-methylhydantoin of I-form crystals manufactured by the known manufacturing method disclosed in the above-mentioned gazettes is dissolved in water and recrystallized whereupon II-form crystals of 5-hydroxy-1-methylhydantoin can be prepared. Since 5-hydroxy-1-methylhydantoin is very highly soluble in water, the ratio of 5-hydroxy-1-methylhydantoin to water which is a recrystallization solvent is preferably about 2:1 (by weight) although the ratio may be appropriately increased or decreased. In the recrystallization, the appropriate amount of water is added to 5-hydroxy-1-methylhydantoin followed by heating at about 50° C. or higher to dissolve and then the solution is cooled to precipitate the crystals whereupon II-form crystals is obtained. The II-form crystals of the present invention is a crystal form which is not produced by recrystallization from organic solvents other than water.

Figure 1:
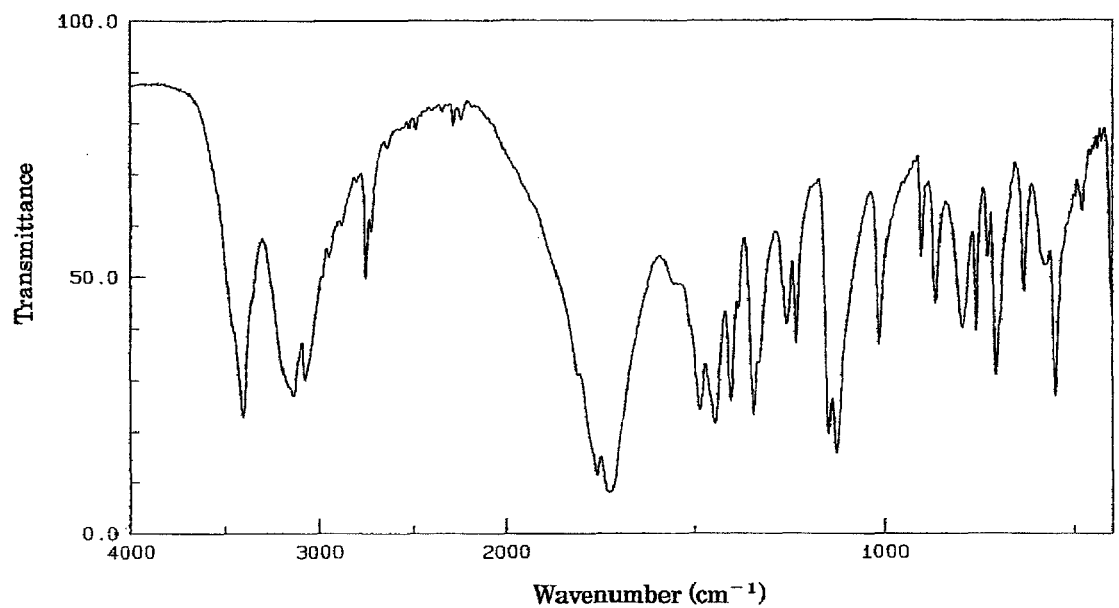
FIG. 1 is an example of infrared absorption spectrum of the II-form crystals of 5-hydroxy-1-methylhydantoin of the present invention as measured by a potassium bromide disk method in Infrared Spectrophotometry using a Fourier-transform infrared spectrophotometer.

The conventional I-form crystals obtained by recrystallization from organic solvents such as acetone and ethyl acetate and the novel II-form crystals obtained by recrystallization from water can be distinguished by infrared absorption spectrum or X-ray diffraction. A method for measurement of infrared absorption spectrum is a method frequently used as a confirmation test for drugs and, for example, it can be carried out according to "Infrared Spectrophotometry" mentioned in the Japanese Pharmacopoeia (14th edition). When the measurement is carried out by a potassium bromide disk method of Infrared Spectrophotometry using Fourier-transform infrared spectrophotometer according to the Japanese Pharmacopoeia, the II-form crystals of the present invention shows an infrared absorption spectrum having a characteristic absorption peaks near 3406 $cm^{-1}$, near 3138 $cm^{-1}$, near 795 $cm^{-1}$ and near 727 $cm^{-1}$ which are different from those of I-form crystals. An example of infrared absorption spectra of 5-hydroxy-1-methylhydantoin of II-form crystals is shown in FIG. 1. With regard to representative absorption peaks, there are noted absorption bands near 3406, 3138, 3074, 2750, 1726, 1485, 1446, 1404, 1344, 1257, 1232, 1126, 1014, 903, 866, 795, 758, 727, 704, 633 and 550 $cm^{-1}$.

Figure 2:
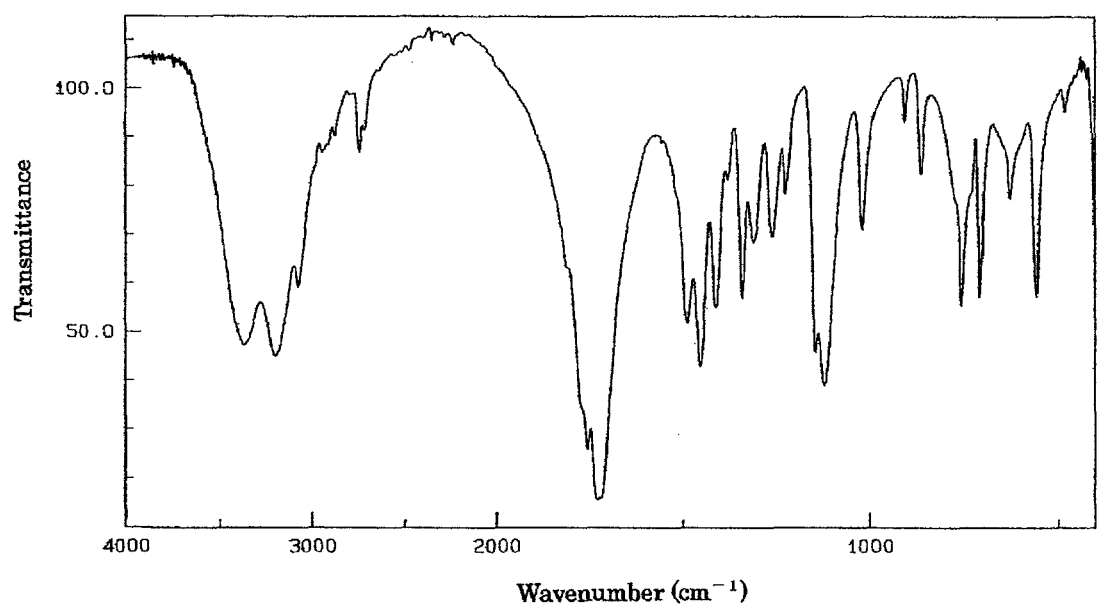
FIG. 2 is an example of infrared absorption spectrum of the I-form crystals of 5-hydroxy-1-methylhydantoin which is a known crystal form as measured by a potassium bromide disk method in Infrared Spectrophotometry using a Fourier-transform infrared spectrophotometer.

On the contrary, the I-form crystals of 5-hydroxy-1-methylhydantoin shows infrared absorption spectrum having characteristic absorption peaks near 3361 $cm^{-1}$, near 3197 $cm^{-1}$ and near 1309 $cm^{-1}$. An example of infrared absorption spectra of the I-form crystals is shown in FIG. 2. With regard to representative absorption peaks, there are noted absorption bands near 3361, 3197, 3074, 2744, 1726, 1487, 1452, 1410, 1340, 1309, 1261, 1225, 1120, 1018, 906, 862, 754, 706, 625 and 555 $cm^{-1}$.

In the above-mentioned wave numbers, representative examples are described and, with regard to the "identification of wave numbers" in infrared absorption spectrum, it has been recognized that "identity within ±0.5% of wave number scale" (stipulations in EP and BP) is almost adequate regardless of the wave number ("Technical Information for Japanese Pharmacopoeia, 2001" edited by Society of Japanese Pharmacopoeia, published by Yakagyo Jihosha (2001)) and identification of the peak wave numbers can be judged according to this standard.

Figure 3:
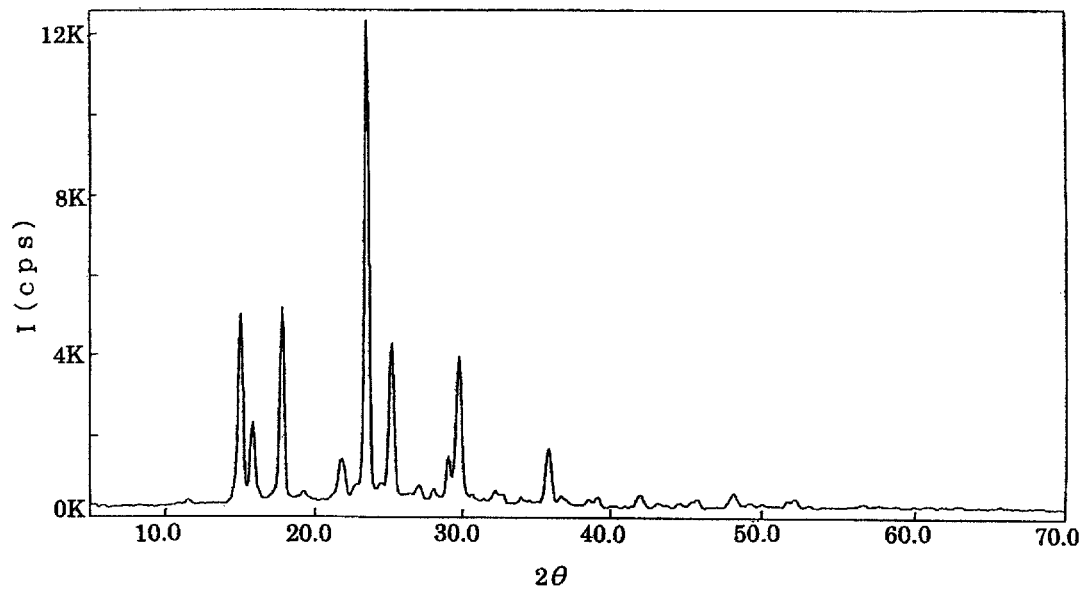
FIG. 3 is an example of X-ray diffraction pattern of the II-form crystals of 5-hydroxy-1-methylhydantoin of the present invention as measured by a X-Ray Powder Diffraction method.

Analysis by X-ray diffraction can be carried out according to the conventional method such as "X-Ray Powder Diffraction" described in the Japanese Pharmacopoeia (14th edition) by the same manner as in the above method for measurement of Infrared Spectrophotometry. Between the II-form crystals of 5-hydroxy-1-methylhydantoin of the present invention and the I-form crystals, there is a clear difference in the X-ray diffraction patterns. When the analysis is carried out with X-ray radiation of wavelength of 1.5405 Å using a copper anticathode, peaks of the diffraction angles 2θ are noted near 15.2, 16.0, 18.0, 21.9, 23.7, 25.4, 29.2, 29.9 and 36.0° in the II-form crystals. Among them, the peaks near 15.2, 18.0, 23.7, 25.4 and 29.9° are the peaks having strong diffraction intensity and can be said to be major peaks. An example of X-ray diffraction patterns of the II-form crystals is shown in FIG. 3.

Figure 4:
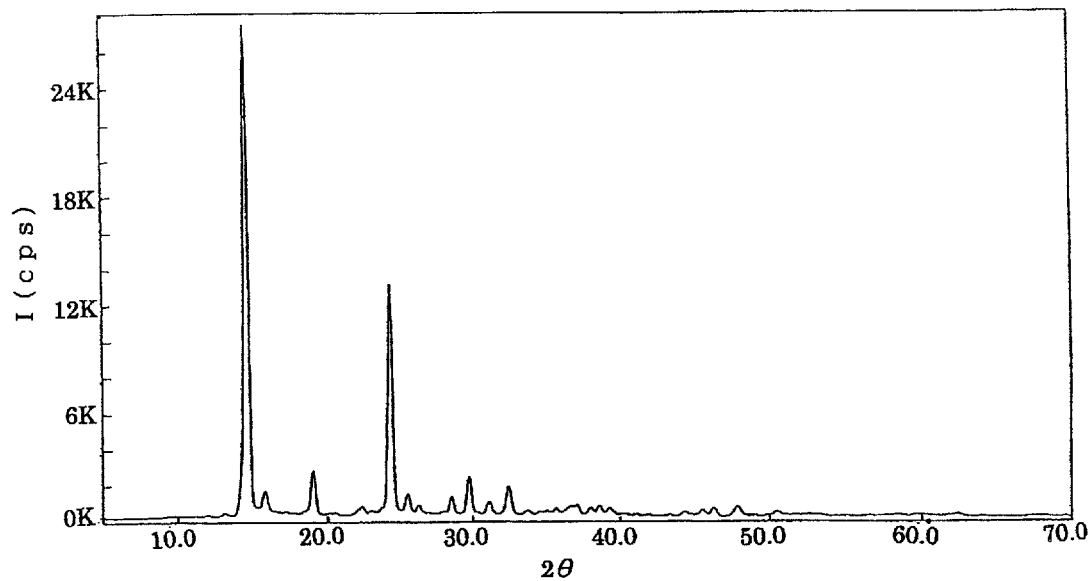
FIG. 4 is an example of X-ray diffraction pattern of the I-form crystals of 5-hydroxy-1-methylhydantoin which is a known crystal form as measured by a X-Ray Powder Diffraction method.

On the other hand, an example of X-ray diffraction patterns of 5-hydroxy-1-methylhydantoin of the I-form crystals is shown in FIG. 4. The major peaks are noted near 14.5, 19.0, 24.4, 29.7 and 32.4° while peaks having weak diffraction intensity are noted near 15.7, 25.5, 28.5 and 31.0°. Incidentally, it is mentioned in the Japanese Pharmacopoeia that, in the same crystal form, the diffraction angle 2θ is usually identical within a range of ±0.2°.

5-Hydroxy-1-methylhydantoin can be manufactured by known manufacturing methods mentioned in the above-mentioned patent gazettes, however, it can be also manufactured by hydrolysis of a brominated product of 1-methylhydantoin. The known manufacturing method is a method where glyoxylic acid alkyl ester is reacted with N-methylurea. Since both 1-methyl and 3-methyl compounds are produced by such method, it is necessary to separate them. However, according to the method of the present invention where a brominated product of 1-methylhydantoin is hydrolyzed, only 1-methyl compound is produced whereby there is an advantage that the manufacturing steps can be simplified and the yield is high. It is so easy to hydrolyze the brominated 1-methylhydantoin, for example, the brominated 1-methylhydantoin is dissolved in water followed by stirring for about one hour at room temperature. In the hydrolysis, hydrogen bromide is produced as a by-product and, when hydrogen bromide remains in the aqueous solution, equilibrium is resulted between the brominated 1-methylhydantoin and 5-hydroxy-1-methylhydantoin whereby, as a result, the yield of 5-hydroxy-1-methylhydantoin which is the aimed compound lowers. Therefore, it is preferred that hydrolysis is carried out together with removal of the resulting hydrogen bromide. As a means for the removal of hydrogen bromide, there may be exemplified a method using a hydrogen bromide scavenger and a method using an anion-exchange resin, and it is preferred to use a method using a hydrogen bromide scavenger in view of cost and labor. An example of the hydrogen bromide scavenger is an epoxy compound represented by the following formula (I).

(I)

[In the formula, R is a lower alkyl group which may be substituted with hydroxyl group(s).]

In the substituent of the above-mentioned formula (I), the lower alkyl is preferably a linear or branched alkyl group having 1 to 6 carbon(s) such as methyl, ethyl, propyl, isopropyl, butyl, isobutyl, sec-butyl, tert-butyl, pentyl, isopentyl, neopentyl, tert-pentyl, hexyl, isohexyl and dimethylbutyl. The above-mentioned lower alkyl group may be substituted with one or more hydroxyl group(s). Specific examples are propylene oxide, 1,2-butylene oxide and glycidol.

In the manufacture of a brominated 1-methylhydantoin, 1-methylhydantoin is added to an appropriate heated solvent such as acetic acid, 1,2-dichloroethane, chloroform, dichloromethane or ethyl acetate, and is brominated using a brominating agent such as bromine. When bromination is carried out by dropping of bromine, reaction temperature and reaction time can be appropriated set depending upon the solvent. As to the solvent, it is preferred to use ethyl acetate in view of safety.

The II-form crystals of 5-Hydroxy-1-methylhydantoin of the present invention is used as a drug material and so can be made into pharmaceutical preparations by a combination with a suitable pharmaceutical carriers or diluents. The compound of this invention may be formulated by any of the conventional methods for providing preparations, such as for oral administrations (e.g. tablets, capsules, powders or liquids) and for parenteral administrations (e.g. for subcutaneous, intravenous, intramuscular, intrarectal and intranasal administrations). En formulating the preparations, the compound of the present invention may be used in the form of its pharmaceutically acceptable salt, and also can be used either solely or jointly together with other pharmaceutically active ingredients.

In the case of preparation for oral administration, the compound of the present invention as it is or together with commonly-used excipients such as a suitable additives (e.g. lactose, mannitol, corn starch, potato starch or potassium citrate) is mixed with binders such as cellulose derivative (e.g. crystalline cellulose or hydroxypropylcellulose), gum arabicum, corn starch or gelatin, disintegrating agents such as corn starch, potato starch or calcium carboxymethylcellulose, lubricating agents such as talc or magnesium stearate, and others including bulking agents moisturizing agents, buffers, preservatives, perfumes and the like to give tablets, diluted powders, granules or capsules. It is also possible, depending upon the type of the disease and the kind of patient, to prepare the pharmaceutical preparations which are other than those which were mentioned already and are suitable for the therapy such as, for example, injections, syrups, suppositories, inhalations, aerosol preparations, eye drops or medicines for external use (e.g. ointments, gels or cataplasms).

The preferred dose of the compound of the present invention may vary depending upon the object to be administered the patient, form of the preparation, method for the administration, term for the administration, etc. and, in order to achieve a desired effect, 20-3,000 mg per day, preferably 50-2,000 mg per day may be usually given to common adults by oral route. In the case of a parenteral administration such as by injection, it is preferred that a level of from 1/3 to 1/10 of the above given dose by oral route is administered.

Preferred embodiments of the present invention are as follows.

(1) II-form crystals of 5-Hydroxy-1-methylimidazolidin-2,4-dione having an infrared absorption spectrum showing characteristic peaks near 3406 cm$^{-1}$, near 3138 cm$^{-1}$, near 795 cm$^{-1}$ and near 727 cm$^{-1}$ when measured by a potassium bromide disk method in Infrared Spectrophotometry.

(2) II-form crystals of 5-Hydroxy-1-methylimidazolidin-2,4-dione having an infrared absorption-spectrum showing peaks near the wave numbers of 3406, 3138, 3074, 2750, 1726, 1485, 1446, 1404, 1344, 1257, 1232, 1126, 1014, 903, 866, 795, 758, 727, 704, 633 and 550 cm$^{-1}$ when measured by a potassium bromide disk method in Infrared Spectrophotometry.

(3) II-form crystals of 5-Hydroxy-1-methylimidazolidin-2,4-dione having an infrared absorption spectrum which is substantially identical with FIG. 1 when measured by a potassium bromide disk method in Infrared Spectrophotometry.

(4) II-form crystals of 5-Hydroxy-1-methylimidazolidin-2,4-dione having an X-ray diffraction pattern showing major peaks of diffraction angles 2θ near 15.2, 18.0, 23.7, 25.4 and 29.9° when measured by X-Ray Powder Diffraction Method.

(5) II-form crystals of 5-Hydroxy-1-methylimidazolidin-2,4-dione having an X-ray diffraction pattern showing peaks of diffraction angles 2θ near 15.2, 16.0, 18.0, 21.9, 23.7, 25.4, 29.2, 29.9 and 36.00 when measured by X-Ray Powder Diffraction Method.

(6) II-form crystals of 5-Hydroxy-1-methylimidazolidin-2,4-dione having an X-ray diffraction pattern which is substantially same as in FIG. 3 when measured by X-Ray Powder Diffraction Method.

(7) The II-form crystals of 5-Hydroxy-1-methylimidazolidin-2,4-dione as mentioned in one of the above (1) to (6) which contains substantially no residual organic solvent.

(8) A drug for renal failure containing the II-form crystals of 5-Hydroxy-1-methylimidazolidin-2,4-dione as mentioned in one of the above (1) to (7) as an effective ingredient.

(9) A process for the production of the II-form crystals of 5-Hydroxy-1-methylimidazolidin-2,4-dione which is characterized in using water as a solvent for recrystallization.

(10) The process for the production according to the above (9), wherein the recrystallization is carried out using about one-half amount (ratio by weight) of water to 5-hydroxy-1-methylimidazolidin-2,4-dione.

(11) II-form crystals of 5-Hydroxy-1-methylimidazolidin-2,4-dione obtained by the process for the production according to the above (9) or (10).

(12) II-form crystals of 5-Hydroxy-1-methylimidazolidin-2,4-dione mentioned in one of the above (1) to (7) obtained by the process for the production according to the above (9) or (10).

(13) A process for the production of 5-hydroxy-1-methylimidazolidin-2,4-dione, characterized in that, a brominated product of 1-methylhydantoin is hydrolyzed.

(14) The process for the production of 5-hydroxy-1-methylimidazolidin-2,4-dione according to the above (13), wherein the hydrolysis is carried out in the presence of an epoxy compound represented by the above-mentioned formula (I).

(15) The process for the production according to the above (14), wherein the epoxy compound in which R in the formula (I) is a lower alkyl group is used.

(16) The process for the production according to the above (15), wherein the epoxy compound in which R is a methyl group is used.

(17) The process for the production according to the above (15), wherein the epoxy compound in which R is an ethyl group is used.

(18) The process for the production according to the above (14), wherein the epoxy compound in which R in the formula (I) is a lower hydroxyalkyl group is used.

(19) The process for the production according to the above (18), wherein the epoxy compound in which R is a hydroxymethyl group is used.

The present invention will be more specifically illustrated by referring to Examples as shown hereunder although the present invention is not limited by them at all.

EXAMPLES

In the following Examples, an example of process for the production of 5-hydroxy-1-methylhydantoin and its II-form crystals of the present invention will be described in more detail. Incidentally, in the following examples, the measurements were carried out using the following instruments. Infrared absorption spectrum was measured by a potassium bromide disk method using Fourier-transform infrared spectrophotometer (Horiba) of FT-200 type. Measurement of X-ray powder diffraction was carried out with X-ray radiation of wavelength of 1.5405 Å by a copper anticathode using X-ray powder diffraction apparatus (Rigaku Denki) of Geiger flex RAD-IA type. Sample for the measurement was prepared in such a manner that crystals were placed on a glass plate and paraffin paper was placed thereon followed by pressing by hand. Melting point was measured using a melting point measuring apparatus (Yamato Kagaku) of MP-21 type. Nuclear magnetic resonance spectrum ($^1$H-NMR) was measured by a nuclear magnetic resonance apparatus (Bruker) of ARX-500 type by using TMS ($\delta$=0) as an internal standard substance. In the measurement of the residual organic solvent, gas chromatograph of GC-15A type (Shimadzu) was used.

Reference Example 1

5-Hydroxy-1-methylhydantoin was synthesized by a method mentioned in the Japanese Patent Laid-Open No. Sho-60-18373 and then acetone was used a solvent for recrystallization to give I-form crystals of 5-hydroxy-1-methylhydantoin. An example of infrared absorption spectrum chart of the resulting I-form crystals is shown in FIG. 2, and an example of the resulting X-ray diffraction pattern is shown in FIG. 4.

The residual organic solvent (acetone) in the resulting I-form crystals was measured by a capillary gas chromatography (Headspace method). As a result of measurements were carried out for 4 lots and amounts of the residual organic solvent (acetone) were 1660±150, 1430±253, 1621±70 and 1336±144 ppm.

Example 1

Process for the Production of II-Form Crystals of 5-hydroxy-1-methylhydantoin

To 105 kg of the I-form crystals of 5-hydroxy-1-methylhydantoin obtained in Reference Example 1 was added about one-half volume (50 liters) of water and the content was dissolved by heating at about 55° C. After filtering off the insoluble matter, the solution was cooled to recrystallize whereupon 63.6 kg of II-form crystals of 5-hydroxy-1-methylhydantoin were obtained. Infrared absorption spectrum of the resulting II-form crystals was measured by a potassium bromide disk method and, as mentioned above, there were noted infrared absorption spectrum having peaks near 3406 $cm^{31\ 1}$, near 3138 $cm^{-1}$, near 795 $cm^{-1}$ and near 727 $cm^{-1}$ (FIG. 1) which were different from those of the I-form crystals. As a result of analysis by X-ray powder diffraction method, peaks of diffraction angle 2θ of the II-form crystals were noted near 15.2, 16.0, 18.0, 21.9, 23.7, 25.4, 29.2, 29.9 and 36.0° (FIG. 3).

When the residual organic solvent used during the process of purification such as acetone in the resulting II-form crystals was measured by a capillary gas chromatography (direct injection method), it was not more than the detection limit of 1 ppm.

Example 2

Process for the Production of II-Form Crystals of 5-hydroxy-1-methylhydantoin Using Brominated 1-methylhydantoin 1) Bromination of 1-methylhydantoin 1-Methylhydantoin (230 kg) was added to 920 liters of ethyl acetate, 329 kg of bromine were dropped thereinto for 10 hours with heating the temperature of the reaction solution to keep at 65 to 80° C., and the mixture was stirred at the same temperature for 0.5 hour. After confirming the disappearance of 1-methylhydantoin by means of an HPLC, the solvent was evaporated in vacuo until the remaining volume became about 460 liters. To the residue were added 460 liters of toluene and the mixture was concentrated again in vacuo until the remaining volume became about 460 liters. Such an operation was carried out twice to azeotropically remove the residual water, 230 liters of toluene were added thereto and the mixture was allowed to stand at room temperature for 12 hours. Brominated 1-methylhydantoin precipitated therefrom was filtered off to give 374 kg of wet crystals.

Melting point: 133~136° C.

$^1$H-NMR (acetone-$d_6$) $\delta$: 2.93 (s, 3H), 6.39 (s, 1H)

2) Synthesis of Crude Crystals of 5-hydroxy-1-methylhydantoin Using Propylene Oxide as a Hydrogen Bromide Scavenger Wet crystals (374 kg) of brominated 1-methylhydantoin were dissolved in 390 liters of purified water and 141 kg of propylene oxide were dropped thereinto for 2 hours where the temperature of the reaction solution was kept at 20° C. or lower. The mixture was stirred at room temperature for 1 hour and, after confirmation of disappearance of the brominated 1-methylhydantoin by means of an HPLC, the solvent was evaporated in vacuo. Acetone (880 liters) was added to the precipitated crystals, the mixture was heated to dissolve, the solvent was evaporated in vacuo until the remaining volume became about 450 liters and the precipitated crystals upon cooling were filtered off. Drying in vacuo was conducted at 40° C. and an operation of recrystallization from acetone was repeated once again to give 180 kg of crude crystals of 5-hydroxy-1-methylhydantoin.

3) Production of II-Form Crystals of 5-hydroxy-1-methylhydantoin

Crude crystals (180 kg) of 5-hydroxy-1-methylhydantoin were dissolved in 84 liters of pure water with warming, insoluble matter was filtered off and the filtrate was stirred with brine cooling. At that time, crystallization may be accelerated by adding seeds of purified II-form crystals. The precipitated crystals separated were filtered off and dried in vacuo at 40° C. to give 100 kg of II-form crystals of 5-hydroxy-1-methylhydantoin. Infrared absorption spectrum and X-ray diffraction patterns of the resulting II-form crystals of 5-hydroxy-1-methylhydantoin were identical with those in Example 1 and confirmed to be the same crystal form. When the residual organic solvent used during the purifying step in the resulting II-form crystals was measured by a capillary gas chromatography method (a direct injection method), it was a detection limit of 1 ppm or less as same as in the case of Example 1.

Melting point: 136° C.

$^1$H-NMR (DMSO-d$_6$) δ: 2.74 (s, 3H), 4.97 (d, 1H, J=8.8 Hz), 6.85 (d, 1H, J=8.8 Hz), 10.73 (s, 1H)

Example 3

Production of 5-hydroxy-1-methylhydantoin Using 1,2-butylene Oxide or Glycidol as a Hydrogen Bromide Scavenger (1) After 4.83 g of brominated 1-methylhydantoin obtained in the same manner as in 1) of Example 2 were dissolved in 5 ml of ice-cooled distilled water, 2.6 ml of 1,2-butylene oxide were dropped thereinto. The mixture was stirred at room temperature for 1 hour and, after confirming the disappearance of brominated 1-methylhydantoin by HPLC, the solvent was evaporated in vacuo. After an operation of adding ethyl acetate to the residue and evaporating it in vacuo was repeated for three times, ethyl acetate was added to the precipitated crystals followed by maturing for 1 hour. The crystals were filtered off and dried in vacuo at 40° C. to give 2.62 g (yield: 81%) of crude crystals of 5-hydroxy-1-methylhydantoin.

(2) After 4.83 g of brominated 1-methylhydantoin obtained in the same manner as in 1) of Example 2 were dissolved in 5 ml of ice-cooled distilled water, 2.0 ml of glycidol were dropped thereinto. The mixture was stirred at room temperature for 1 hour and, after confirming the disappearance of brominated 1-methylhydantoin by HPLC, the solvent was evaporated in vacuo. After an operation of adding ethyl acetate to the residue and evaporating it in vacuo was repeated for three times, ethyl acetate/diethyl ether (1:1) was added to the precipitated crystals followed by maturing for 1 hour. The crystals were filtered off and dried in vacuo at 40° C. to give 2.51 g (yield: 77%) of crude crystals of 5-hydroxy-1-methylhydantoin.

Example 4

Measurement of Bulk Density

Each 40 g of the I-form crystals produced in Reference Example 1 and the II-form crystals produced in Example 2 were placed in a graduated cylinder to measure the volume whereby bulk density was calculated. After that, each graduated cylinder was lightly patted by hand under the same condition until the volume of the dry powder became unchanged so that the crystals were tightly packed. The volume after the tight packing was measured and bulk density was calculated. An example of the result is shown in Table 1.

TABLE 1

| Sample | Bulk Density Before Tight Packing (g/mL) | Bulk Density After Tight Packing (g/mL) |
|---|---|---|
| I-form Crystals | 0.35 | 0.46 |
| II-form Crystals | 0.54 | 0.64 |

INDUSTRIAL APPLICABILITY

As apparently from the above result, the organic solvent used in the purifying step considerably remains in the I-form crystals while, in the II-form crystals obtained by recrystallization from water, residue of the organic solvent is not more than the detection limit (1 ppm), and so the II-form crystals of the present invention is a crystal form where there is substantially no residue of organic solvent. As mentioned already, it is preferred for the compounds used as drugs that the toxic residual solvents are to be made as little as possible. Especially in patients suffering from renal failure, waste products and toxic substances are not excreted but accumulated in the body due to the disorder of renal functions and, therefore, toxic residual solvent is to be made as little as possible in anti-renal-failure drugs. However, as mentioned above, considerable amount of solvent for recrystallization remains when 5-hydroxy-1-methylhydantoin is recrystallized from an organic solvent such as acetone or ethyl acetate and, therefore, that is not preferred as bulk material for drugs, particularly the drug for renal failure, which are demanded to be highly safe. Accordingly, there has been a demand for obtaining a purified product which substantially contains no residual solvent and the II-form crystals of the present invention has a desirable characteristic satisfying the demand.

In addition, in the II-form crystals of the present invention, the bulk density is higher than in the I-form crystals and the volume for the same weight is small whereby it is now possible to manufacture small tablets and so to provide the tablets which are easily administered to patients. The advantage of high bulk density is also advantageous in terms of storage and handling when production is conducted in an industrial scale. Further, it has been found after various handlings of both II-form crystals and I-form crystals that adhesion onto the solid surface such as glass wall is lower in the II-form crystals than in the I-form crystals. Accordingly, in the case of the II-form crystals, loss during the manufacture can be reduced and labor such as cleaning and checking for removal of adhered things to the manufacturing devices and apparatuses can be reduced as well.

As such, in the novel II-form crystals of 5-hydroxy-1-methylhydantoin obtained by recrystallization from water, there is substantially no residue of organic solvent and, moreover, it has preferred characteristics in the manufacture such as sufficient stability, high bulk density which is advantageous for the production of pharmaceutical preparations and low adhesion whereby it is very highly useful as a material for drugs such as a drug for renal failure where a high safety is demanded.

The invention claimed is:

1. A process for the production of 5-hydroxy-1-methylimidazolidin-2,4-dione, comprising hydrolyzing a brominated product of 1-methylhydantoin.

2. The process for the production of 5-hydroxy-1-methylimidazolidin-2,4-dione according to claim 1, wherein the hydrolysis is carried out in the presence of an epoxy compound represented by the following formula (I)

(I)

wherein R is a lower alkyl group, or a lower alkyl group which is substituted with at least one hydroxyl group.

3. The process for the production according to claim 2, wherein R is a lower alkyl group.

4. The process for the production according to claim 3, wherein R is a methyl group.

5. The process for the production according to claim 3, wherein R is an ethyl group.

6. The process for the production according to claim 2, wherein R is a lower hydroxyalkyl group.

7. The process for the production according to claim 6, wherein R is a hydroxymethyl group.

8. The process for the production according to claim 1, wherein the hydrolysis of the brominated product is carried out together with removal of hydrogen bromide.

9. The process for the production according to claim 1, wherein the hydrolysis of the brominated product is carried out in the presence of a hydrogen bromide scavenger to remove hydrogen bromide produced during the hydrolysis.

10. The process for the production according to claim 8, wherein the removal of hydrogen bromide is by an anion-exchange resin.

* * * * *

UNITED STATES PATENT AND TRADEMARK OFFICE
CERTIFICATE OF CORRECTION

| | | |
|---|---|---|
| PATENT NO. | : 7,858,806 B2 | Page 1 of 1 |
| APPLICATION NO. | : 12/498967 | |
| DATED | : December 28, 2010 | |
| INVENTOR(S) | : Okamoto et al. | |

It is certified that error appears in the above-identified patent and that said Letters Patent is hereby corrected as shown below:

On the Cover page, under (63) Related U.S. Application Priority Data, of the printed patent, replace "Continuation of application No. 10/508,496, filed as application No. PCT/JP03/04497 on Apr. 9, 2003, now Pat. No. 7,569,701." with -- Continuation of Application No. 10/508,496, filed on Apr. 9, 2003, now Pat. No. 7,569,701, which is a 371 U.S. national stage application of International Application No. PCT/JP03/04497 filed on April 9, 2003. --.

Signed and Sealed this
Twentieth Day of September, 2011

David J. Kappos
*Director of the United States Patent and Trademark Office*